United States Patent [19]

Rock

[11] 4,439,319

[45] Mar. 27, 1984

[54] RECEPTACLE FOR THE COLLECTION OF MEDICAL SPECIMENS AND THE LIKE

[76] Inventor: John G. Rock, 130 Forest Rd., Davenport, Iowa 52803

[21] Appl. No.: 398,741

[22] Filed: Jul. 16, 1982

[51] Int. Cl.³ .............................................. B01D 29/02
[52] U.S. Cl. .................................... 210/238; 210/248; 210/256; 210/489; 210/517; 604/406
[58] Field of Search .............. 210/806, 237, 238, 248, 210/256, 261, 262, 321.1, 321.2, 321.3, 330, 337, 338, 342, 489, 492, 515, 516, 517, 518, 927, 476, 477, 479; 604/4, 5, 6, 356, 406; 422/101, 102

[56] References Cited

U.S. PATENT DOCUMENTS

| | | | |
|---|---|---|---|
| 47,460 | 4/1865 | Rossman | 210/238 |
| 4,131,549 | 12/1978 | Ferrara | 210/518 |
| 4,318,803 | 3/1982 | Holmgren | 210/927 |
| 4,321,139 | 3/1982 | Auclair | 210/927 |
| 4,326,959 | 4/1982 | Ferrara | 210/516 |

Primary Examiner—Charles N. Hart
Assistant Examiner—Wanda L. Millard
Attorney, Agent, or Firm—Henderson & Sturm

[57] ABSTRACT

A double-walled receptacle formed of inner and outer open-topped containers, the inner one fitting within the outer so as to be upwardly removable therefrom. The inner container is divided into upper and lower compartments by a foraminous partition and the lower part of the inner container wall has a plurality of fluid drain apertures below the partition. The partition is mounted so as to be easily removable upwardly from the inner container. The partition receives the solid, semi-solid portions, etc., of the specimens and fluids escape into the lower compartment. Flushing media used in the collection of the specimens escapes via the drain apertures and is caught by the outer container. A removable cover closes the open tops of both containers.

6 Claims, 3 Drawing Figures

RECEPTACLE FOR THE COLLECTION OF MEDICAL SPECIMENS AND THE LIKE

BACKGROUND OF THE INVENTION

Many forms of receptacles have been known for use in the collection of medical specimens from both humans and animals. A particular example of the use of specimens in the diagnosis of disease is the practice of currettage in the case of intrauterine disease. There are of course areas other than emdometrial instances where contents or portions of a body are collected for diagnostic purposes. In substantially any case, what is collected or withdrawn will normally include solid, semi-solid, etc., portions (e.g., tissue) and associated fluids, including whatever liquid flushing medium is employed. The present invention provides a receptacle of liquid-impervious material in which these several substances are separated, primarily by a screen or like foraminous partition within a container. Materials of lesser substance than that retained by the screen pass through the screen into a compartment below the screen and excess flushing medium is drained off into an outer container within which the inner, partitioned container is relatively loosely fitted. A common cover closes both containers and the receptacle and its contents are easily handled for subsequent examination, testing, etc.

DETAILED DESCRIPTION OF A PREFERRED FORM OF THE INVENTION

Figure 1:
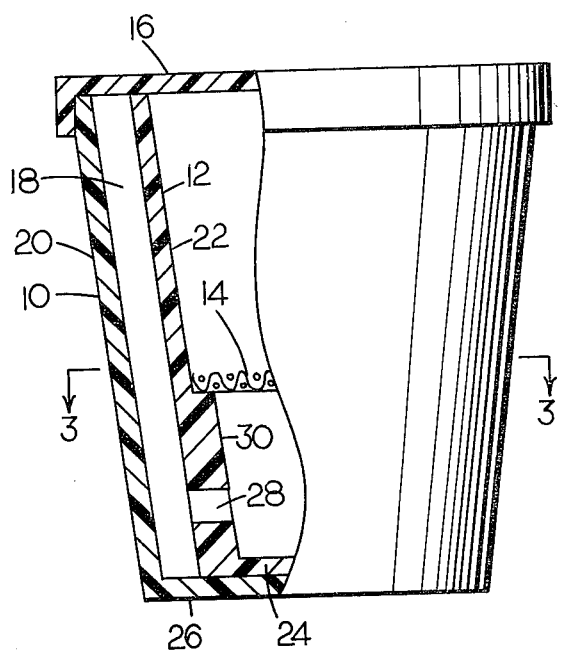
FIG. 1 is an exploded perspective showing the basic elements of the receptacle.
Figure 2:
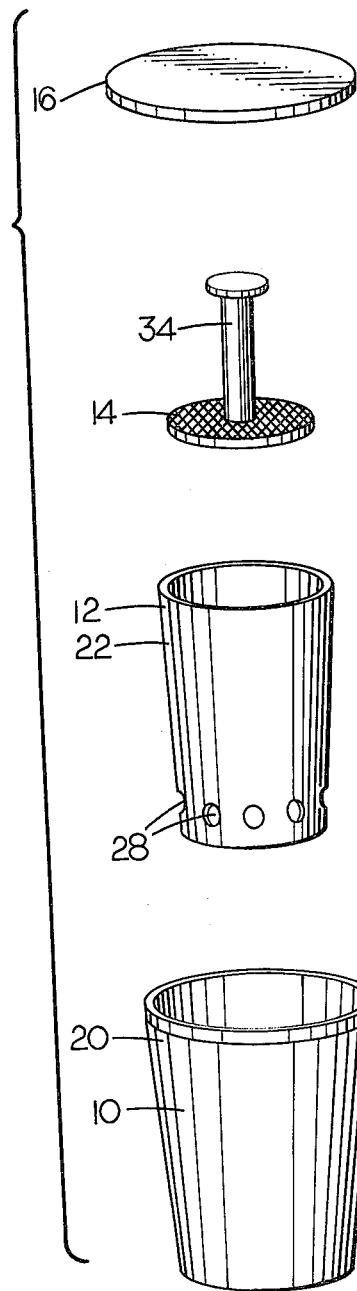
FIG. 2 is a partial vertical section through the assembled receptacle.
Figure 3:
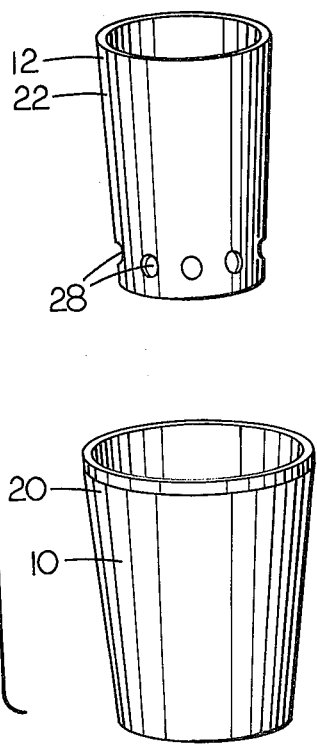
FIG. 3 is a partial section on the line 3—3 of FIG. 2.
Figure 3:
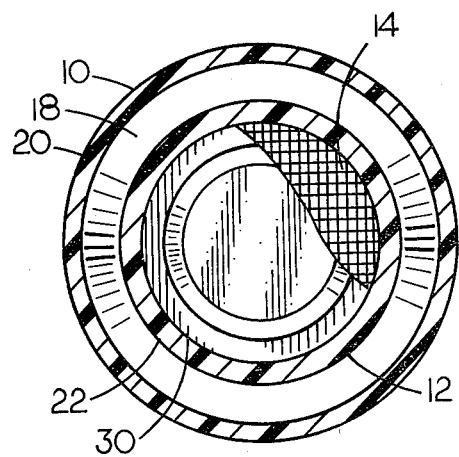

The receptacle is of multi-part construction and comprises an outer container 10, an inner container 12, an inter transverse partition 14 and a cover 16 common to both containers. All parts of the receptacle, with the exception of the partition, are constructed of liquid-impervious material, at least within the degree expected from the intended use and life of the parts. Any of the well-known materials for this purpose may be used. The dimensions of the receptacle may vary according to the expected or intended use thereof. The present disclosure is based on a receptacle in which the outer container is approximately the size of a typical "throwaway" beverage cup and the inner container is sized so as to nest within the outer container and so that the cover, when in place on the outer container, also closes the inner container. The cover may have any type of removable association with the outer container; e.g., snap-over fit, screw-on, etc., depending upon the designer's choice. Nesting of the inner container within the outer is such that a space 18 may exist between the outer container annular wall 20 and the inner container annular wall 22. The inner container has a bottom 24 which may conveniently rest on the bottom 26 of the outer container.

An exception to the liquid-imperviousness of the inner container is made by the provision of liquid or fluid drain aperture means, here comprising a plurality of uniformly circumferentially spaced apertures 28 formed in a lower portion of the periphery of the inner container annular wall. The partition 14 may be formed of any type of preferably non-corrosive foraminous or screen material, the mesh of which, like the dimensions of the receptacle, depends upon the consistency, fluidity, etc., of the specimens, etc., with which the receptacle is to be used, the amount of handling, the length of storage and the like.

The partition is disposed across the lower part of the inner container and is circular here to adapt itself to the roundness of the container. Both containers are here shown as being of inverted truncated-cone shape, but here again that is not material to the invention. It does, however, make quick selection and nesting, as well as easy removal of the inner container from the outer. The partition is held in spaced relation above the inner container floor or bottom by downward-limiting abutment means, here an interiorly thickened portion 30 of the inner container wall. This portion preferably extends peripherally about the interior of this wall and forms a ledge on which the partition may rest while in use and from which the partition may be removed when necessary or desired. A handle 34 may be attached to the partition to facilitate removal and replacement thereof.

The drain apertures 28 are spaced slightly above the inner container bottom so as to trap a certain amount of liquid draining off from the partition, yet the apertures will permit excessive flushing fluids to escape into the space 18. Initially, the outer container may hold a measured quantity of preservative or like medium of which many types are known in the art.

It will be understood that only a preferred embodiment of the invention has been disclosed here and that many modifications may be made therein without departing from the spirit and scope of the invention.

I claim:

1. Receptacle means for use in the collection of medical specimens and the like, comprising an open-toppd outer container liquid-impervious material having a bottom and an annular wall, an open-topped inner container disposed removably within the outer container and having a bottom and annular wall, said inner container being formed of liquid-impervious material except for the provision of at least one fluid drain aperture in its wall spaced relatively closely above its bottom, a foraminous partition intermediate the top and bottom of the inner container and dividing said inner container into upper and lower compartments, said partition being spaced above the drain aperture, means supporting the partition in the inner container for upward removal thereof from said inner container, and cover means for removably covering the open top of the outer container and thus also closing the open top of the inner container.

2. The receptacle means of claim 1, in which the means supporting the partition includes a portion integral with the inner container wall and forming downward limiting abutment means.

3. The receptacle of claim 2, in which the abutment means is a peripheral ledge about the inner surface of the inner container wall.

4. The receptacle of claim 2, in which the abutment means is an interiorly thickened part of the inner container wall.

5. The receptacle means of claim 1, in which there are a plurality of fluid drain apertures spaced peripherally about the inner container wall in uniformly spaced relation above the inner container bottom.

6. The receptacle means of claim 1, in which the partition includes, attached thereto, a handle accessible through the open tops of the containers for facilitating removal and replacement of the partition.

* * * * *